United States Patent [19]
Kalman

[11] Patent Number: 5,886,162
[45] Date of Patent: *Mar. 23, 1999

[54] LIPOPHILIC DIAKYLAMINOMETHYLENE PRODRUG DERIVATIVES FOR THE INHIBITION OF REPLICATION OF VIRUSES

[75] Inventor: Thomas I. Kalman, East Amherst, N.Y.

[73] Assignee: Research Foundation of State University of New York, Albany, N.Y.

[*] Notice: The term of this patent shall not extend beyond the expiration date of Pat. No. 5,051,498.

[21] Appl. No.: 763,781

[22] Filed: Sep. 23, 1991

Related U.S. Application Data

[63] Continuation-in-part of Ser. No. 431,286, Nov. 3, 1989, Pat. No. 5,051,498.

[51] Int. Cl.$^6$ .......................... C07H 19/00; A01N 43/54; C07D 237/00
[52] U.S. Cl. .......................... 536/22.1; 536/26.1; 514/49; 514/50; 514/256; 514/261; 544/1; 544/242; 544/264; 544/269
[58] Field of Search ............................... 514/49, 50, 256, 514/261; 544/1.1, 269, 242, 264; 536/22.1, 26.1

[56] References Cited

U.S. PATENT DOCUMENTS

| | | | |
|---|---|---|---|
| 3,957,803 | 5/1976 | Bodor et al. | 260/295 |
| 4,036,845 | 7/1977 | Bodor et al. | 260/295 |
| 4,046,899 | 9/1977 | Bodor | 424/266 |
| 4,061,722 | 12/1977 | Bodor | 424/273 |
| 4,061,753 | 12/1977 | Bodor et al. | 424/253 |
| 4,069,322 | 1/1978 | Bodor et al. | 424/241 |
| 4,085,214 | 4/1978 | Higuchi et al. | 424/253 |
| 4,160,099 | 7/1979 | Bodor | 560/110 |
| 4,163,053 | 7/1979 | Neustadt et al. | 424/230 |
| 4,213,978 | 7/1980 | Bodor et al. | 424/241 |
| 4,221,787 | 9/1980 | Bodor et al. | 424/241 |
| 5,051,498 | 9/1991 | Kalman | 536/23 |

*Primary Examiner*—Ponnathapura Achutamurthy
*Attorney, Agent, or Firm*—Crossetta & Associates

[57] ABSTRACT

This invention provides new lipophilic dialkylaminomethylene prodrugs, particularly dialkylaminomethylene 2',3'-dideoxynucleoside compounds and pharmaceutical compositions comprising said compounds which inhibit the replication of viruses.

11 Claims, No Drawings

LIPOPHILIC DIALKYLAMINOMETHYLENE PRODRUG DERIVATIVES FOR THE INHIBITION OF REPLICATION OF VIRUSES

This application is a continuation-in-part of U.S. patent application Ser. No. 07/431,286, filed Nov. 3, 1989, now U.S. Pat. No. 5,051,498.

This invention was made in part with government support under Grant Number 1R01AI2725-01A1 awarded by the National Institutes of Health, Department of Health and Human Services, and the government has certain rights herein.

BACKGROUND OF THE INVENTION

Anti-viral agents, such as the 2', 3'-dideoxynucleosides, have been seen as being of increasing importance in the treatment of disease. Such agents, are believed to function as chain-terminators, after intracellular phosphorylation to their 5'-triphosphates and incorporation into newly synthesized viral DNA by reverse transcriptase. It is generally believed that the lack of the 3' hydroxy group, essential for phosphodiester bond formation, contributes to their function. Such agents are thought to inhibit viral reverse transcriptase much more strongly than cellular DNA polymerase α. An example of such agent is AZT, the 3'-azido derivative of thymidine, which is believed to exert its anti HIV activity through this mechanism.

As clinical experience with agents such as AZT grows, it has been recognized that though the drug does not appear to cure AIDS, it does provide considerable therapeutic benefit to patients with AIDS or AIDS related complex (ARC). Its major drawback however is its severe bone marrow toxicity, which can lead to anemia, leukopenia and neutropenia. Although AZT is orally effective, it is expensive, has a short half-life and must be taken continuously every several hours at a dose of 250 mg or more.

Other nucleoside analogs, particularly 2', 3'-dideoxycytidine (ddC) and 2', 3'-dideoxyadenosine, have been found to be effective in inhibiting viral replication in this group of agents. Phase I and II trials with ddC has revealed much less bone marrow suppression with this agent as compared to AZT, however, peripheral neuropathy poses a special problem and appears to comprise the dose limiting toxicity of this drug.

Recently, AIDS patients were given weekly alternating regimes of AZT and ddC with encouraging results. Since the two drugs have different toxicity profiles, this mode of administration may permit adequate recovery from toxicity without compromising anti-viral activity in some patients. Other combination modalities of AZT and ddC are in clinical trials.

Currently available nucleoside analogs exhibit therapeutic benefits but also have many recognized shortcomings including short plasma half-life, insufficient penetration into the central nervous system, low therapeutic index, low potential for metabolic activation and/or high susceptibility to catabolism, and the emergence of clinical resistance. Thus, there is a continuing demand for more effective antiviral agents for use in the treatment of AIDS and related viral infections. To overcome these difficulties, a variety of prodrugs of antiviral agents have been synthesized and examined for therapeutic values.

For purposes of this specification by the term "prodrug" as used herein is meant a derivative of an active form of a known composition which derivative, when administered to a mammal, is gradually converted to the active form to produce a better therapeutic response and/or a reduced toxicity level.

The term "transient" as used herein describes the action of time-dependent conversion to the active form of a composition from its prodrug derivative, by chemical hydrolysis or other means including but not limited to enzymatic action, in such a manner that the active form is released from the derivative and the residue which remains of the derivative is essentially nontoxic and/or is metabolized to nontoxic metabolic by-products.

An object of this invention is to provide new, transient lipophilic dialkylaminomethylene prodrug derivatives, useful as chemotherapeutic agents which exhibit prolonged duration of action and decreased cellular and systemic toxicities.

A further object of this invention is to provide new lipophilic dialkylaminomethylene prodrug derivatives demonstrating an increased ability to cross biological membranes, particularly the "blood brain barrier."

A still further object of the invention is to provide new dialkylaminomethylene prodrug derivatives demonstrating varying degrees of lipophilicity and susceptibility to hydrolysis, permitting the optimization of pharmacokinetic properties and therapeutic effectiveness.

A still further object of the invention is to provide new compounds suitable as topical, in vitro, disinfectants.

These and other objects of this invention will become apparent from the following description of the invention.

DESCRIPTION OF THE INVENTION

This invention relates to new lipophilic prodrug derivatives comprising a dialkylaminomethylene group as a component part thereof and to compositions comprising these derivatives.

In accordance with this invention, new dialkylaminomethylene derivatives are provided having the formula:

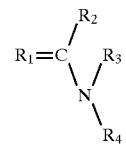

wherein $R_1$ is a chemotherapeutic agent comprising an exocyclic nitrogen atom for divalent attachment to an aminomethylene group at least one of aromatic ring and heterocyclic ring, and two or more electronegative atoms capable of accepting hydrogen bonds; $R_2$ is selected from the group consisting of hydrogen or alkyl, alkenyl and alkynyl group containing from 1 to about 20 carbon atoms; $R_3$ and $R_4$ are the same or different and are independently selected from the group consisting of alkyl, alkenyl and alkynyl group of 1 to about 20 carbon atoms, cycloalkyl group containing 3–6 carbon atoms and aralkyl group; and salts thereof.

Preferred compounds are those of the formula:

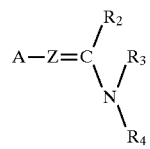

wherein $R_2$, $R_3$ and $R_4$ are as previously described; Z is a pyrimidine or purine base structure, having an exocyclic nitrogen atom for divalent attachment to a dialkylaminomethylene group, said base structure being selected from the group consisting of cytosine, 5-azacytosine, dihydro-5-azacytosine, 6-azacytosine, 3-deazacytosine, 5-chlorocytosine, 5-fluorocytosine, 5-hydroxymethylcytosine, isocytosine, 5-methylcytosine, adenine, guanine, and the 1-deaza, 2-aza, 2-fluoro, 3-deaza, 7-deaza, 8-aza, 2,8-diaza, 7-deaza-8-aza, and 9-deaza derivatives of said structure; and, A is a structure of the formula:

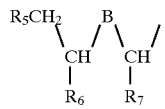

Wherein B is selected from the group consisting of oxygen, sulfur and $CH_2$; $R_5$ is selected from the group consisting of hydroxy, phosphate, phosphonate and phosphonomethyl; $R_7$ is hydrogen; $R_6$ is selected from the group consisting of hydrogen, hydroxy, hydroxymethyl, phosphate, phosphonate and phosphonomethyl; providing, $R_6$ and $R_7$ can combine to form a heterocyclic ring in which instance $R_7$ is selected from the group consisting of CH, $CH_2$, CHF and $CF_2$ while $R_6$ is selected from the group consisting of CH, $CH_2$, CHF, $CHN_3$, $CHNH_2$, oxygen, sulfur and nitrogen; and salts thereof.

Within the broad recitation of the invention, the most preferred compounds are of the formula:

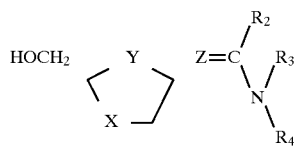

wherein $R_2, R_3$ nd $R_4$ are as previously described; X is selected from the group consisting of CHF, $CHN_3$, $CHNH_2$, oxygen and sulfur; Y is selected from the group consisting of oxygen, sulfur and $CH_2$; Z is a pyrimidine or purine base structure, having an exocyclic nitrogen atom for divalent attachment to a dialkylaminomethylene group, said base structure being selected from the group consisting of cytosine, 5-azacytosine, dihydro-5-azacytosine, 6-azacytosine, 3-deazacytosine, 5-chlorocytosine, 5-fluorocytosine, 5-hydroxymethylcytosine, isocytosine, 5-methylcytosine, adenine, guanine, and the 1-deaza, 2-aza, 2-fluoro, 3-deaza, 7-deaza, 8-aza, 2,8-diaza, 7-deaza-8-aza, and 9-deaza derivatives of said structure; and salts thereof.

Especially preferred compounds comprise the N-dialkylaminomethylene compounds of the structure.

The invention comprises the aforesaid compounds, pharmaceutically acceptable salts thereof and compositions containing the compounds, particularly disinfectants and pharmaceutical compositions.

In addition to the foregoing, the invention includes a process for increasing the lipophilicity of a chemotherapeutic agent comprising divalently attaching, a dialkylaminomethylene group of the formula:

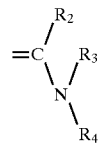

wherein $R_2$ is selected from the group consisting of hydrogen or alkyl, alkenyl and alkynyl group containing from 1 to about 20 carbon atoms; $R_3$ and $R_4$ are the same or different and are independently selected from the group consisting of alkyl, alkenyl and alkynyl group of 1 to about 20 carbon atoms, cycloalkyl group containing 3–6 carbon atoms and aralkyl group; to an exocyclic nitrogen atom of a chemotherapeutic agent having at least one of aromatic ring and heterocyclic ring, and providing two or more electronegative atoms are capable of accepting hydrogen bonds.

Within the following description, references to a pyrimidine base structure comprises reference to cytosine, while reference to a purine base structure comprises reference to adenine and guanine.

The $R_1$ chemotherapeutic base structure to which the dialkylaminomethylene component is attached can comprise a multiplicity of known chemotherapeutic structures providing it comprises at least one or both of an aromatic ring or a heterocyclic ring, as well as a nitrogen, exocyclic to said rings, to which the dialkylaminomethylene group can divalently attach. Particularly preferred are the anti-viral agents.

Applicant has found that when a chemotherapeutic agent, comprises an exocyclic amino group and two or more electronegative atoms capable of accepting hydrogen bonds, the agent typically has a limited water solubility. Generally, water solubility of a compound would be expected to decrease when alkyl groups are attached to the molecule. Unexpectedly, it has been found that when certain alkyl containing moieties are properly attached to the exocyclic amino group of certain chemotherapeutic agents, the agent can maintain and even increase its water solubility. Further, applicant has found that select alkyl containing moieties, when properly attached to the chemotherapeutic agent, so augment the lipophilicity of the agent that the combined effect is a significant increase in the lipophilicity of the agent without significant negative effect upon the water solubility of the compound.

By increasing the lipophilicity of the agent, with retention of water solubility, the pharmokinetic properties of the agent can be modified to allow controlled passage of the drug through the various tissue and cell barriers thus providing for enhanced drug delivery to target sites, which may include storage sites, for sustained release of the drug. At the same time, the required concentration of physiological fluid can be achieved.

Generally it is preferred that the chemotherapeutic agent comprise a pyrimidine or purine base structure, attached to an acyclic or cyclic substituent. A preferred cyclic structure is one such as a sugar selected from 2, 3-dideoxy-D-ribofuranose or 2, 3-dideoxy-3-fluoro-D-ribofuranose, which is covalently bonded in β-linkage via its $C_1$ to the $N_1$ or $N_9$ of the pyrimidine or purine base structure, respectively, to form the corresponding nucleoside.

Within the description of the compounds of the invention, particularly the designations $R_1$, $R_2$, $R_3$ and $R_4$, by the term alkyl, alkenyl and alkynyl is meant alkane, alkene, and alkyne hydrocarbon subsituents having from 1 to about 20 carbon atoms. Substituents can be straight chained, or branched and include isomers thereof. Thus the term alkyl includes methyl, ethyl, n-propyl, i-propyl, n-butyl, i-butyl, t-butyl, pentyl, hexyl, heptyl and the like up to about 20 carbon atoms. Similarly, the term alkenyl includes unsaturated hydrocarbons having one or more double bonds therein such as ethene, propene, butene, pentene and the like up to about 20 carbon atoms, while the term alkynyl includes hydrocarbons having one or more triple bonds therein such as acetylene, methyl acetylene, ethyl acetylene and the like up to about 20 carbon atoms.

Within the recitation of the invention, by the term aralkyl is meant an aromatic ring linked through one or more methylene groups. Thus, the term aralkyl includes benzyl, phenylethyl and the like up to about 20 carbon atoms. Similarly, by the term cycloalkyl is meant a saturated monocyclic hydrocarbon containing up to about 10 carbon atoms and preferably from about 3 to about 5 carbon atoms.

By the term aromatic ring is meant cyclic aromatic groups such as benzene, naphthalene, anthracene, phenanthrene, quinoline, indole and the like up to about 12 carbon atoms. By the term heterocyclic ring is meant compounds comprising an oxygen, sulfur, nitrogen and the like within a ring structure. Preferred heterocyclic rings include pyridine, pyrimidine, diazepine, imidazol and the like having 5 to 7 carbon atoms. The chemotherapeutic agent must comprise an exocyclic nitrogen for divalent attachment to the aminomethylene group of the structure of the invention.

In the recitation of the invention $R_7$ will be hydrogen unless $R_6$ and $R_7$ combine to form a heterocyclic ring. In the latter instance R7 participates in the ring as CH, $CH_2$, CHF or $CHF_2$ depending upon unsaturation or saturation of the ring. Similarly, the selection of $R_6$ is different when it stands alone than when combined with $R_7$ in a heterocyclic ring and in the latter circumstance can in addition to the selections for $R_7$ be $CHN_3$, $CHNH_2$, oxygen and sulfur.

$R_2$, $R_3$ and $R_4$ are attached, through the methylene linking group, to an exocyclic nitrogen on the chemotherapeutic agent substituent. In the preferred compounds the attachment is through an exocyclic nitrogen on a pyrimidine or purine base structure, forming a series of side chain-bearing nucleoside derivatives. It has been discovered that the introduction of dialkylaminomethylene substituents at the exocyclic $NH_2$ group of parent dideoxynucleosides, that have anti-viral activity, leads to a series of nitrogen substituted prodrugs exhibiting decreased toxicity and the ability to selectively enhance lipophilicities favorable for efficient penetration into the central nervous system.

Typical dialkylamino substituted nucleoside derivatives falling within the structure of the claimed invention include $N^4$-dimethylaminomethylene-2', 3'-dideoxy-3'-fluorocytidine (DDFC); $N^4$-diethylaminomethylene-2', 3'-dideoxy-3'-fluorocytidine; $N^4$-diisopropylamino-methylene-2', 3'-dideoxy-3'-fluorocytidine; $N^4$-di-n-butylaminomethylene-2', 3'-dideoxy-3'-fluorocytidine; $N^4$-morpholino-methylene-2', 3'dideoxy-3'-fluorocytidine; $N^4$-piperidino-methylene-2', 3'-dideoxy-3'-fluorocytidine; $N^4$-2,6-dimethyl-piperidinomethylene-2', 3'-dideoxy-3'-fluorocytidine; $N^4$-dimethylaminomethylene-2', 3'-dideoxy-3'-fluorocytidine; $N^4$-diethylaminomethylene-2', 3'-dideoxycytidine; $N^4$-diisopropyl-aminomethylene-2', 3'-dideoxycytidine; $N^4$-di-n-butylamino-methylene-2', 3'-dideoxycytidine; $N^4$-morpholinomethylene-2', 3'-dideoxycytidine; $N^4$-pyrrolidino-methylene-2', 3'-dideoxycytidine $N^4$-piperidinomethylene-2', 3'-dideoxycytidine; $N^4$-2,6-dimethylpiperidinomethylene-2', 3'-dideoxycytidine; $N^6$-dimethylaminomethylene-2', 3'-dideoxyadenosine; $N^6$-diisopropylaminomethylene-2', 3'-dideoxyadenosine and the like.

Generally, the $R_1$ anti-viral component of the invention can be selected from many readily available anti-viral drugs, providing the drug comprises an exocyclic nitrogen in its structure that can be divalently attached to a substituted aminomethylene group in accord with the invention. Generally, the attachment of the methylene to the $R_1$ component can be attained through various known routes, the simplest being generally to react an exocyclic amine group of an $R_1$ anti-viral drug, with the desirable substituted formamide acetal group in accord with the following schematic.

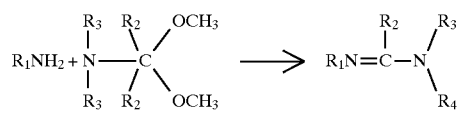

When the $R_1$ component comprises the 2', 3'-dideoxynucleosides and 2', 3'-dideoxy-3'-fluoronucleosides of the preferred compounds, such as for example, 2', 3'-dideoxycytidine (ddC), the compounds of the invention may be prepared according to the method of Prisbe and Martin as described in Synth. Commun. 15, 401 (1985) the disclosure of which is incorporated by reference herein.

Briefly, this method involves the conversion of N, 5'-dipivaloyl-2'-deoxycytidine obtained by treatment of 2'-deoxycytidine with pivaloyl chloride, to its 3'-thionocarbonateusing N,N'-thiocarbonyl-diimidazole, typically in DMF at 80° C. Subsequent reduction using tri-n-butyltin hydride followed by ammonolytic deprotection leads to the product.

An alternative synthetic method is disclosed by Lin et al., J. Med. Chem. 30, 440 (1987), starting with 2', 3'-dideoxycytidine, and involves ammonolysis of the intermediate acetylated 4-triazolylpyrimidinone derivative.

A method for the preparation of 2', 3'-dideoxy-3'-fluorocytidine from 5'-trityl-2'deoxycytidine, using the fluorinating reagent DAST, was recently described by Herdewijn et al. at J. Med. Chem. 30, 1270 (1987), the disclosure of which is hereby also incorporated by reference herein.

The general procedure for preparation of the dialkylaminomethylene cytosine nucleosides modified at the exocyclic amino group on the pyrimidine base is disclosed by Zemlicka et al. at Coll. Czech. Chem. Commun. 32, 3159 (1967). The process comprises reacting one equivalent of the nucleoside with an excess of the dialkyl-formamide dimethylacetal in dry DMF (or dimethylacetamide, DMSO or a similar polar solvent) in the absence of moisture. The contents are allowed to stir overnight and then the solvent and excess reagent are removed by rotary evaporation. The syrupy residue obtained is then subjected to crystallization, typically from ethanol or ethanol-ether mixture, to obtain the desired nucleoside.

In a typical example of such procedure, previously dried 2', 3'-dideoxycytidine (153 mg, 0.724 mmoles) which was previously prepared by the literature procedures described above is treated with diisopropylformamide dimethylacetal (1.27 g, 7.24 mmoles) in anhydrous DMF (2 mL) under an argon atmosphere. The product is stirred overnight and thereafter solvent and excess reagent are removed by rotary evaporation. The syrupy residue remaining is crystallized from ethanolether to give pale lemon-colored crystals (185 mg, 79%) of diisopropylaminomethylene 2', 3'-dideoxycytidine.

If the dimethylacetal starting material is unavailable, it may be prepared by reacting one equivalent of the appropriate formamide with an equivalent of dimethylsulfate at about 85° C. for about 60 hours to form the dialkylformamide dimethylsulfate adduct in accord with Bredereck et al., Chem. Ber. 101, 41 (1968). The adduct is next treated dropwise with an equivalent of sodium methoxide in methanol at about -5 to about 0 degrees Celsius for a period of 4–5 hours. The contents are then distilled under vacuum to obtain the desired acetal.

In a typical reaction sequence, diisopropylformamide (50 g, 0.386 moles) is treated with dimethylsulfate (48.76 g, 0.386 moles), and the contents are stirred at 85° C. for 60 hours to form the adduct. A solution of sodium methoxide (0.386 moles of sodium in 138 mL of anhydrous methanol) is added dropwise over a period of 4–5 hours maintaining the temperature at about −5° C. The excess methanol is removed by rotary evaporation under an argon atmosphere and the remaining contents are vacuum distilled under an argon atmosphere to give 38 g (60%) of the diisopropylformamide dimethylacetal.

As is well recognized by those skilled in the art pertaining to the instant invention, any number of systematic variations in the structure of the methylene substituted exocyclic amino side chain may be introduced using known methods similar to those set forth above. By altering the nature of the diaklyl substituent in the terminal N-atom of the side chain, with an appropriate substituent, a wide variety of prodrugs can be attained that exhibit increasing or decreasing variations in their lipophilicity, thus permitting the selection of that degree of lipophilicity which is optimal for enhancing the drug's ability to cross a particular biological membrane and the intended site of action for the drug. The systematic variation of differing substituents allows the optimization of pharmacokinetic parameters leading to the enhancement of therapeutic effectiveness.

The nucleosides of the present invention can be converted into the acid salts via reaction with an appropriate acid. Typical acids include organic and inorganic acids such as aliphatic, alicyclic and araliphatic acids, aromatic and heterocyclic acids, mono- and poly-basic acids, sulfonic acids, as well as various of the well known mineral acids. Examples of suitable, physiologically acceptable salt forming acids are formic, acetic, propionic, pivalic, diethylacetic, oxalic, malonic, succinic, maleic, lactic, tartaric, malic, aminocarboxylic, sulfamic, benzoic, salicylic, phenylpropionic, citric, gluconic, ascorbic, nicotinic, isonicotinic methanesulfonic, p-toluene-sulfonic, sulfuric, nitric, hydrochloric, phosphoric acids and the like.

The transient prodrug compounds of this invention are useful as inhibitors of viruses and retroviruses, and particularly, as inhibitors of the AIDS, HIV retrovirus. In such respect, the 2', 3'-dideoxycytosine, adenine and guanine nucleoside component of the compound appear to maintain their demonstrated viral inhibiting properties, with the methylene substituted side chain enhancing the drug's ability to cross the appropriate biological membrane. Once administered, the methylene substituted side chain undergoes spontaneous hydrolysis at physiologic pH leading to a sustained release of the parent nucleoside analog.

The compounds of this invention can be used in oral, injection and perfusion treatment procedures and can be used in admixture with pharmaceutically acceptable organic or inorganic carriers suitable for parenteral, external or topical applications. It should be understood that carriers suitable for use with the present compounds are those that will not react in a deleterious manner with the compounds. Suitable, pharmaceutically acceptable carriers include, but are not limited to water, salt solutions, alcohols, vegetable oils, polyethylene glycols, gelatin, lactose, amylose, magnesium stearate, talc, silicic acid, paraffins, perfume oils fatty acid mono and diglycerides, hydroxy alkylcelluloses, poly-vinyl pyrrolidone and the like.

The pharmaceutical preparations may also optionally include auxiliary agents such as lubricants, preservatives, stabilizer, wetting agents, emulsifiers, buffers, salts for influence of osmotic pressure, flavoring, coloring and like substances which are nonreactive with the active compounds. In parenteral applications, oily or aqueous sonicated solutions are particularly useful, as well as suspensions and emulsions.

Enteric application can be realized by compounding the compounds as tablets, capsules with carriers and binders of talc, carbohydrate or the like. Sustained release properties may be included by the utilization of differentially degradable coatings such as microencapsulation, multiple coatings or the like.

As topical applications, the compounds are employed in compositions having consistencies ranging from viscous to solid non-sprayable, utilizing pharmaceutically acceptable carriers commonly used in topical applications. Suitable formulations include but are not limited to solutions, suspensions, creams, ointments, emulsions, powders, liniments, salves and the like which may include such auxiliary agents as preservatives, stabilizers, wetting agents, buffers and the like.

Sprayable aerosol formulations incorporating the active compounds of this invention are also within the purview of topical application, the active compound preferably in combination with a solid or liquid inert carrier packaged in a suitable dispensing container, pressurized by means of a volatile, normally gaseous propellant, such as freon and the like.

In topical formulations, the active compounds of this invention are typically utilized at concentrations of from about 1 to about 10 percent by weight.

The novel compounds of the present invention are generally administered to mammals, including but not limited to man in a retroviral inhibiting effective daily dosage of the active compound from about 1 mg/kg animal body weight to about 10 mg/kg animal body weight of the organism being treated. In general, large animals require less of any pharmaceutical compound per kilogram of body weight than smaller animals. The dosage amount may be administered in multiple daily dosages.

Generally, the dosage in man is lower than for small warm blooded mammals such as mice. A dosage unit may comprise a single compound of the invention or mixtures thereof with other compounds of the invention, or other compounds useful in the treatment procedure.

It is to be appreciated that the actual preferred and effective amounts of the compounds of this invention used will vary according to the specific compound being utilized, the particular compositions formulated, the application mode, as well as the particular sites and organism being subjected to treatment. Factors which generally tend to modify drug action will be taken into consideration by those of skill in the art, such factors as age, weight, sex, diet, times and methods of administration, reaction sensitivities, severity of the condition treated, etc. Optimal application rates for any given set of conditions can be determined by those skilled in the art employing conventional dosage determination tests, considering the foregoing guidelines.

The following specific embodiments are set forth to illustrate the preparation and use of the compounds of the present invention and are not to be construed as limitative. Unless otherwise indicated, all parts and percentages are by weight.

EXAMPLE 1

Synthesis of $N^4$-dimethylaminomethylene-2', 3'-dideoxy-3'-fluorocytidine.

Previously dried 2', 3'-dideoxy-3'-fluorocytidine (300mg, 1.3 mmoles) was treated with dimethylformamide dimethylacetal (0.45 g, 3.8 mmoles) in anhydrous DMF (5 mL) under a nitrogen atmosphere. The contents were stirred overnight and the solvents removed by rotary evaporation. The syrupy residue remaining was crystallized from ethanol to give white crystals (276 mg, 75%) of the product $N^4$-dimethylaminomethylene-2', 3'-dideoxy-3'-fluorocytidine, having a melting point of 203° C. Elemental analysis confirmed the structure as being $C_{12}H_{17}FN_4O_3$ with a molecular weight of 284.30 (Calcd. C, 50.70; H, 6.03; N, 19.70: Found C, 50.68; H, 6.05; N, 19.68). Infrared and $H^1$NMR spectral analysis was consistent with the aforesaid structure. Ultraviolet spectra, in ethanol was determined to be $\delta_{max}$317 nm, $\epsilon$36,200 and $\delta_{min}$242 nm, $\epsilon$2,040. Optical rotation was determined to be $[\alpha]D+130.5°$ (c=1.00, EtOH).

EXAMPLE 2

A series of compounds were produced in accord with the method of Example 1 with various substitutions of 2' deoxycytidine at the $N^4$ position of the dialkylaminomethylene side chain. Comparison of retention times obtained by reverse phase high pressure liquid chromatography (HPLC) is set forth in Table 1.

Because of economic considerations 2'-deoxycytidine, was used as the parent nucleoside for comparison purposes in this study. The results shown in Table 1 revealed a marked increase in lipophilicity in the series 1–9, as reflected by the increase in retention time.

The rates of hydrolysis of the different derivatives appear to depend greatly on the structure of the substituent introduced at the exocyclic $NH_2$ group. For example, the half-life ($t_{1/2}$) of $N^4$-dimethylaminomethylene 2'-dideoxycytidine (compound 3 in Table 1) is 5 hours at 37° in 10 mM K-phosphate buffer at pH 7.4, as determined by UV spectroscopy and HPLC analysis. Under the same conditions, $N^4$-diisopropylamino-methylene-2'-deoxycytidine (compound 7 in Table 1) has a $t_{1/2}$=3 days. Thus, there is an order of magnitude difference in the rate of hydrolysis of these two side chains. The variations in the susceptibility to hydrolysis provide another parameter for the optimization of the pharmacokinetic profile.

EXAMPLE 3

Significant activity of $N^4$-dimethylaminomethylene-2', 3'dideoxy-3'-fluorocytidine (DDFC, NSC D614989) and of $N^4$-dimethylaminomethylene-2', 3'-dideoxycytidine (DAM-ddC, NSC D621506) against human immunodeficiency virus (HIV-1, strain LAV) has been demonstrated by results obtained from the National Cancer Institute's In-Vitro Testing Program.

The protocol used in NCI's Developmental Therapeutics Program AIDS antiviral drug screening program involves plating of susceptible human "host" cells with and without virus in microculture plates, adding various concentrations of test material, incubating the plates for seven days (during which time infected, non-drug treated control cells are largely or totally destroyed by the virus), and then determining the number of remaining viable cells using a calorimetric endpoint. The dose dependent antiviral activity and cytotoxicity were determined and plotted on a graph illustrated as FIG. 1.

Two parameters are extracted from the curves illustrated in FIG. 1: the EC50, representing the concentration of drug that results in a 50% reduction of the viral cytopathic effect; and the IC50, representing the concentration of drug resulting in 50% cytotoxicity (growth inhibition derived from the normal, uninfected cultures). An in-vitro therapeutic index (TI) may be calculated as the ratio ($IC_{50}/EC_{50}$)if both values are obtained.

As shown in FIG. 1, in the anti-HIV drug screen of the National Cancer Institute, DDFC has shown significant antiviral activity in several cell lines. In the CEM cell line, complete protection against HIV was achieved by 8 micromolar DDFC without any cytotoxicity.

In all five different cell lines tested by NCI there was uniformly very little cytotoxicity observed with DDFC and the $IC_{50}$ could not be reached up to 200 $\mu$m, the highest concentration employed. This data is summarized in Table 2.

As shown in FIG. 2, the extent of protection of CEM cells by DDFC against the cytopathic effect of HIV correlated with the decrease in the presence of viral p24 antigen detected by enzyme-linked immunosorbent assay.

In the anti-HIV drug screen, $N^4$-dimethylaminomethylene-2', 3'-dideoxycytidine, likewise, showed significant antiviral activity as demonstrated in FIG. 3.

From the foregoing description, one skilled in the art to which this invention pertains, can easily ascertain the essential features thereof, and can make various changes and modifications to adapt it to various usages and conditions without departing from the spirit and scope thereof.

TABLE 1

General Structure:

N=CH—R (structure with cytosine-like base and deoxyribose sugar bearing CH$_2$OH and OH)

| | COMPOUND | R | RETENTION TIME (min) |
|---|---|---|---|
| 1. | 2'-Deoxycytidine | — | 2.13 |
| 2. | $N^4$-Morpholinomethylene-2'-deoxycytidine | —N(morpholino)O | 3.07 |
| 3. | $N^4$-dimethylaminomethylene-2'-deoxycytidine | —N(CH$_3$)$_2$ | 3.26 |
| 4. | $N^4$-Pyrrolidinomethylene-2'-deoxycytidine | —N(pyrrolidinyl) | 5.16 |
| 5. | $N^4$-Diethylaminomethylene-2'-deoxycytidine | —N(C$_4$H$_5$)$_2$ | 6.44 |
| 6. | $N^4$-Piperidinomethylene-2' deoxycytidine | —N(piperidinyl) | 7.79 |
| 7. | $N^4$-Diisopropylamino-methylene-2'-deoxycytidine | —N[CH(CH$_3$)$_2$]$_2$ | 15.79 |
| 8. | $N^4$-2,6-Dimethylpiperidino-methylene-2'-deoxycytidine | —N(2,6-dimethylpiperidinyl) | 21.81 |
| 9. | $N^4$-Di-n-butylamino-methylene-2'-dioxycytidine | —N(nC$_4$H$_9$)$_2$ | 125 |

TABLE 2

Cytotoxicity of DDFC in the NCI in vitro anti-HIV drug screen

| CELL LINE | DATE OF TEST | $IC_{50}$, $\mu M$ ($\mu g/ml$) |
|---|---|---|
| ATH8 | 9-08-87 | >200(>56) |
| CEM | 1-13-88 | >200(>56) |
| CEM | 1-23-88 | >0.2(>0.055)[a] |
| CEM | 3-15-88 | >200(>56) |
| CEM | 3-25-88 | >200(>56) |
| CEM | 3-16-88 | >200(>56) |
| C3-44 | 3-15-88 | >200(>56) |
| C3-44 | 3-16-88 | >200(>56) |
| LDV-7 | 3-15-88 | >200(>56) |
| LDV-7 | 3-16-88 | >200(>56) |
| LDV-7 | 3-25-88 | >200(>56) |
| MT-2 | 1-29-88 | >200(>56) |
| MT-2 | 3-25-88 | >200(>56) |

[a]Highest concentration tested

What is claimed is:

1. Dialkylaminomethylene derivatives of the formula:

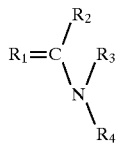

wherein $R_1$ is a chemotherapeutic agent comprising a 5 or 6 member heterocyclic ring, said agent being a nucleoside that is capable of accepting hydrogen bonds and having an exocyclic nitrogen atom which is divalently attached to the aminomethylene group of the structure; $R_2$ is selected from the group consisting of hydrogen or alkyl, alkenyl and alkynyl group containing from 1 to about 20 carbon atoms; $R_3$ and $R_4$ are the same or different and are independently selected from the group consisting of alkyl, alkenyl and alkynyl group of 1 to about 20 carbon atoms, cycloalkyl group containing 3–6 carbon atoms and aralkyl group; and salts thereof.

2. A compound of claim 1 of the formula:

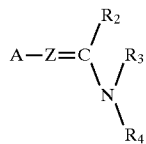

wherein Z is a pyrimidine structure, having an exocyclic nitrogen atom divalently attached to the aminomethylene group of the structure a, said base structure being selected from the group consisting of cytosine, 5-azacytosine, dihydro-5-azacytosine, 6-azacytosine, 3-deazacytosine, 5-chlorocytosine, 5-fluorocytosine, 5-hydroxymethylcytosine, isocytosine, 5-methylcytosine, and the 1-deaza, 2-aza, 2-fluoro, and 3-deaza, derivatives of adenine and guanine; and, A is a structure of the formula:

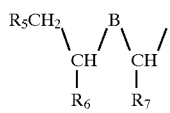

Wherein B is selected from the group consisting of oxygen, sulfur and $CH_2$; $R_5$ is selected from the group consisting of hydroxy, phosphate, phosphonate and phosphonomethyl; $R_7$ is hydrogen; $R_6$ is selected from the group consisting of hydrogen, hydroxy, hydroxymethyl, phosphate, phosphonate and phosphonomethyl; providing, $R_6$ and $R_7$ can combine to form a heterocyclic ring in which instance $R_7$ is selected from the group consisting of CH, $CH_2$, CHF and $CF_2$ while $R_6$ is selected from the group consisting of CH, $CH_2$, CHF, $CHN_3$, $CHNH_2$, oxygen, sulfur and nitrogen; and salts thereof.

3. A compound of claim 1 of the formula:

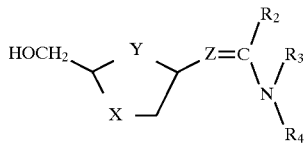

wherein X is selected from the group consisting of CHF, $CHN_3$, $CHNH_2$, oxygen and sulfur; Y is selected from the group consisting of oxygen, sulfur and $CH_2$; Z is a pyrimidine structure, having an exocyclic nitrogen atom divalently attached to the aminomethylene group of the structure, said base structure being selected from the group consisting of cytosine, 5-azacytosine, dihydro-5-azacytosine, 6-azacytosine, 3-deazacytosine, 5-chlorocytosine, 5-fluorocytosine, 5-hydroxymethylcytosine, isocytosine, 5-methylcytosine, and the 1-deaza, 2-aza, 2-fluoro, and 3-deaza, derivatives of adenine and guanine; and salts thereof.

4. A pharmaceutical composition comprising a pharmaceutical carrier and a compound of claim 1.

5. A composition of claim 4 comprising $N^4$-dimethylaminomethylene-2', 3'-dideoxy-3'-fluorocytidine.

6. A composition of claim 4 comprising $N_4$-dimethylaminomethylene-2', 3'-dideoxycytidine.

7. A composition of claim 4 comprising $N^4$-diisopropylaminomethylene-2', 3'-dideoxy-3'-fluorocytidine.

8. A composition of claim 4 comprising $N^4$-diisopropylaminomethylene-2', 3'-dideoxycytidine.

9. A composition of claim 4 comprising $N^6$-dimethylaminomethylene-2', 3'-dideoxyadenosine.

10. A composition of claim 4 comprising $N^6$-diisopropylaminomethylene-2', 3'-dideoxyadenosine.

11. A process for increasing the lipophilicity of a nucleoside chemotherapeutic agent comprising divalently attaching an aminomethylene group of the formula:

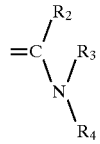

wherein $R_2$ is selected from the group consisting of hydrogen or alkyl, alkenyl and alkynyl group containing from 1 to about 20 carbon atoms; $R_3$ and $R_4$ are the same or different and are independently selected from the group consisting of alkyl, alkenyl and alkynyl group of 1 to about 20 carbon atoms, cycloalkyl group containing 3–6 carbon atoms and aralkyl group; to an exocyclic nitrogen atom of a chemotherapeutic agent having a 5 or 6 member heterocyclic ring that is capable of accepting hydrogen bonds.

* * * * *